(12) United States Patent
Niemtzow

(10) Patent No.: US 11,253,703 B2
(45) Date of Patent: Feb. 22, 2022

(54) ELECTRICAL ACUPTUNCTURE EYE TREATMENT

(71) Applicant: Richard Charles Niemtzow, Alexandria, VA (US)

(72) Inventor: Richard Charles Niemtzow, Alexandria, VA (US)

(*) Notice: Subject to any disclaimer, the term of this patent is extended or adjusted under 35 U.S.C. 154(b) by 211 days.

(21) Appl. No.: 16/511,356

(22) Filed: Jul. 15, 2019

(65) Prior Publication Data

US 2019/0336768 A1 Nov. 7, 2019

Related U.S. Application Data

(62) Division of application No. 15/692,724, filed on Aug. 31, 2017, now Pat. No. 10,406,360.

(60) Provisional application No. 62/393,723, filed on Sep. 13, 2016.

(51) Int. Cl.
*A61N 1/32* (2006.01)
*A61N 1/36* (2006.01)
*A61H 39/08* (2006.01)
*A61F 9/007* (2006.01)
*A61B 18/14* (2006.01)

(52) U.S. Cl.
CPC .......... *A61N 1/36046* (2013.01); *A61F 9/007* (2013.01); *A61H 39/086* (2013.01); *A61N 1/36017* (2013.01); *A61B 2018/1425* (2013.01); *A61H 2201/10* (2013.01); *A61H 2201/5002* (2013.01); *A61H 2205/024* (2013.01)

(58) Field of Classification Search
CPC .................... A61N 1/36046; A61B 2018/1425
See application file for complete search history.

(56) References Cited

U.S. PATENT DOCUMENTS

2012/0130398 A1* 5/2012 Ackermann ....... A61N 1/36142
606/129

* cited by examiner

*Primary Examiner* — Michael J D'Abreu
(74) *Attorney, Agent, or Firm* — Dunlap Bennett & Ludwig, PLLC

(57) ABSTRACT

A system and method for eye treatment. The system and method utilize an electro acupuncture stimulator. The electro acupuncture stimulator includes a positive lead and a negative lead. The system further includes a pair of first needles, a second needle and a diode. The pair of first needles are electrically connected to one of the positive lead and the negative lead. The diode is electrically connected to the other of the positive lead and the negative lead. The second needle is electrically connected to the diode.

15 Claims, 5 Drawing Sheets

// ELECTRICAL ACUPUNCTURE EYE TREATMENT

CROSS-REFERENCE TO RELATED APPLICATION

This application is a divisional of U.S. non-provisional application Ser. No. 15/692,724, filed Aug. 31, 2017, which claims the benefit of priority of U.S. provisional application No. 62/393,723, filed Sep. 13, 2016, the contents of which are herein incorporated by reference.

BACKGROUND OF THE INVENTION

The present invention relates to eye treatment and, more particularly, to a system and method of treating vision degradation using electro-acupuncture.

Aging, genetics and disease can cause degradation of a patient's vision. For example, retinopathies consisting of macular degeneration, diabetic retinopathies, and retinitis pigmentosa all cause degradation of vision.

As can be seen, there is a need for a system and method for improving vision degradation.

SUMMARY OF THE INVENTION

In one aspect of the present invention, a system for eye (s) treatment comprises: an electro acupuncture stimulator comprising of a positive lead and a negative lead; an acupuncture needle electrically connected to a positive lead is inserted into the bony orbital area of the eye and the negative lead from the eye circuit is connected to the appropriate polarity pole of the diode and another wire from the appropriate polarity pole of the diode connects to an acupuncture needle that is inserted superficially into the bony area of the sternum serving as a ground for the entire circuit.

In another aspect of the present invention, a method of eye treatment comprises the steps of: penetrating a patient's skin with one of a pair of first needles at a lower orbital area of a first eye; penetrating the patient's skin with the other of the pair of first needles at a lower orbital area of a second eye; penetrating the patient's skin with a second needle at a sternum; electrically connecting the second needle to a diode; electrically connecting one of a positive lead and a negative lead of an electro acupuncture stimulator to the pair of first needles; electrically connecting the other of the positive lead and the negative lead of the electro acupuncture stimulator to the diode; and powering the electro acupuncture stimulator.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes an electro-acupuncture system and method for improving low vision caused by retinopathies; for example, macular degeneration, diabetic retinopathy and retinitis pigmentosa. The present invention improves patients having very poor eye vision from various types of retinopathies.

The system and method of the present invention includes electrical stimulation of BL1 and Ren17 with an electroacupuncture stimulator at 2-10 Hz. The present invention uses a diode to maintain the current in the retinal area of the eye using bone conduction at the acupuncture points. The present invention includes a unique conduction system using bone of the patient to reach the bony structure surrounding the retina and permitting indirect stimulation. The diode prevents the stimulating current from returning to the sternum area.

Figure 1:
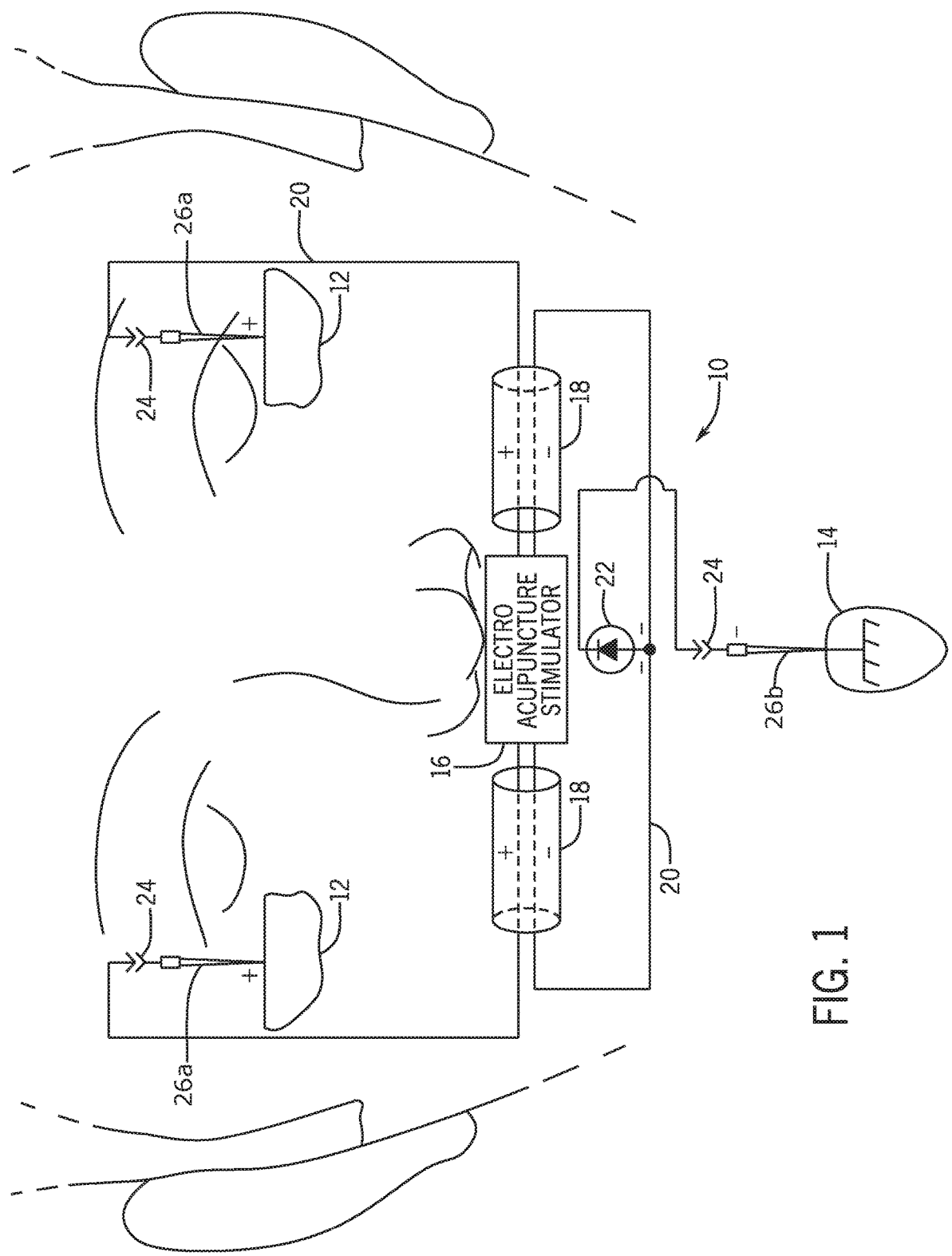
FIG. 1 is a schematic view of an embodiment of the present invention.
Figure 2A:
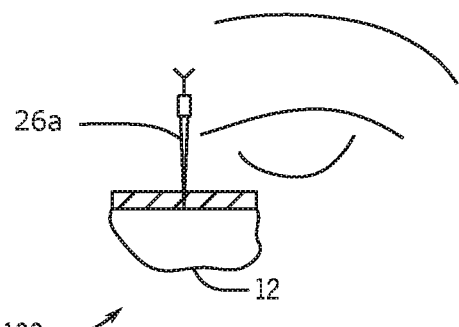
FIGS. 2A-2G are schematic views illustrating steps of an embodiment of a method of the present invention.
Figure 2B:
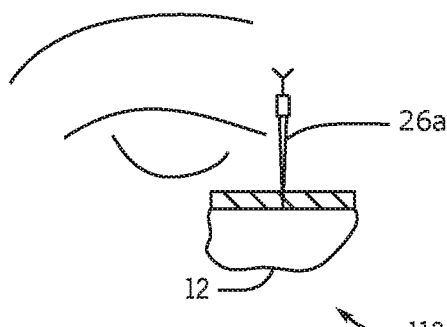
Figure 2C:
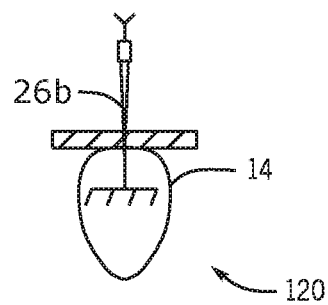
Figure 2D:
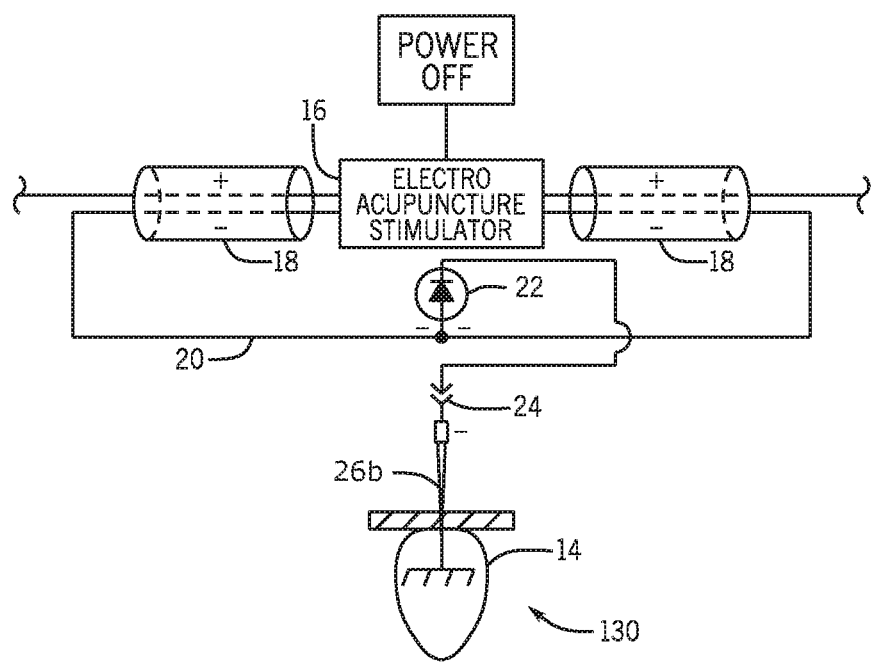
Figure 2E:
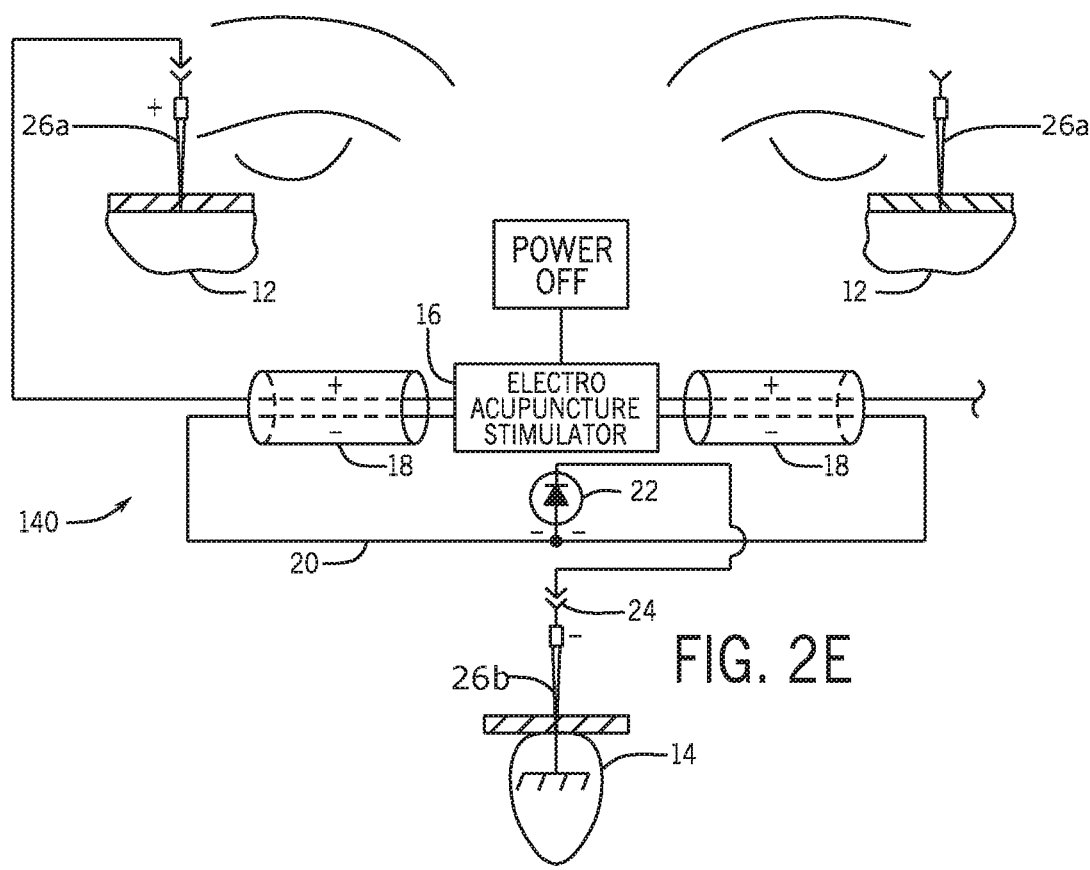
Figure 2F:
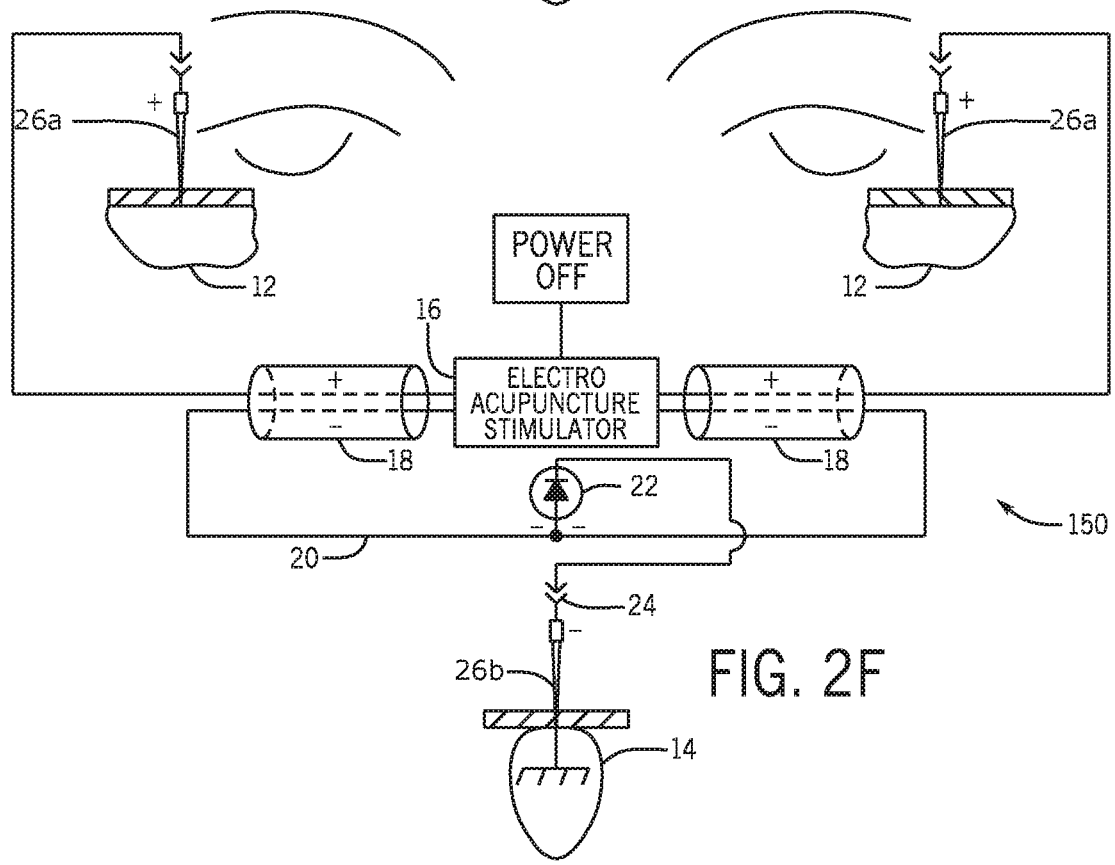
Figure 2G:
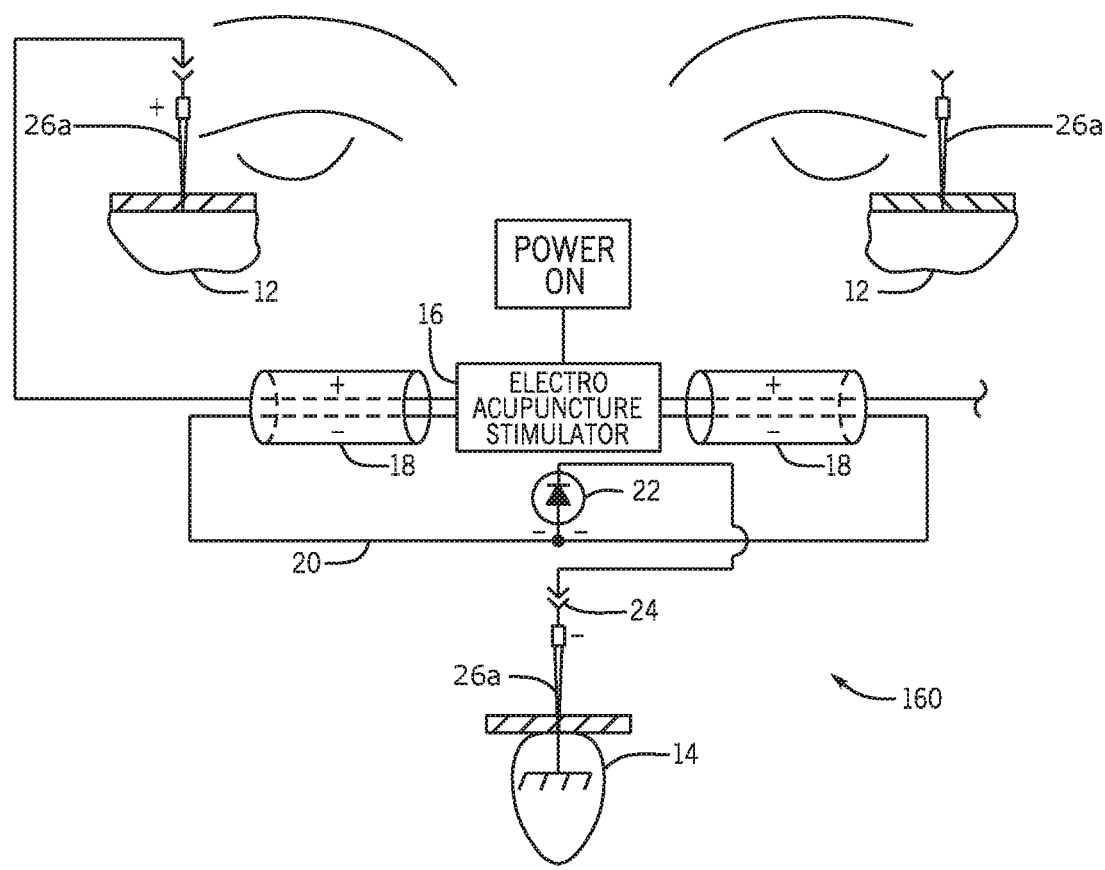
Figure 3:
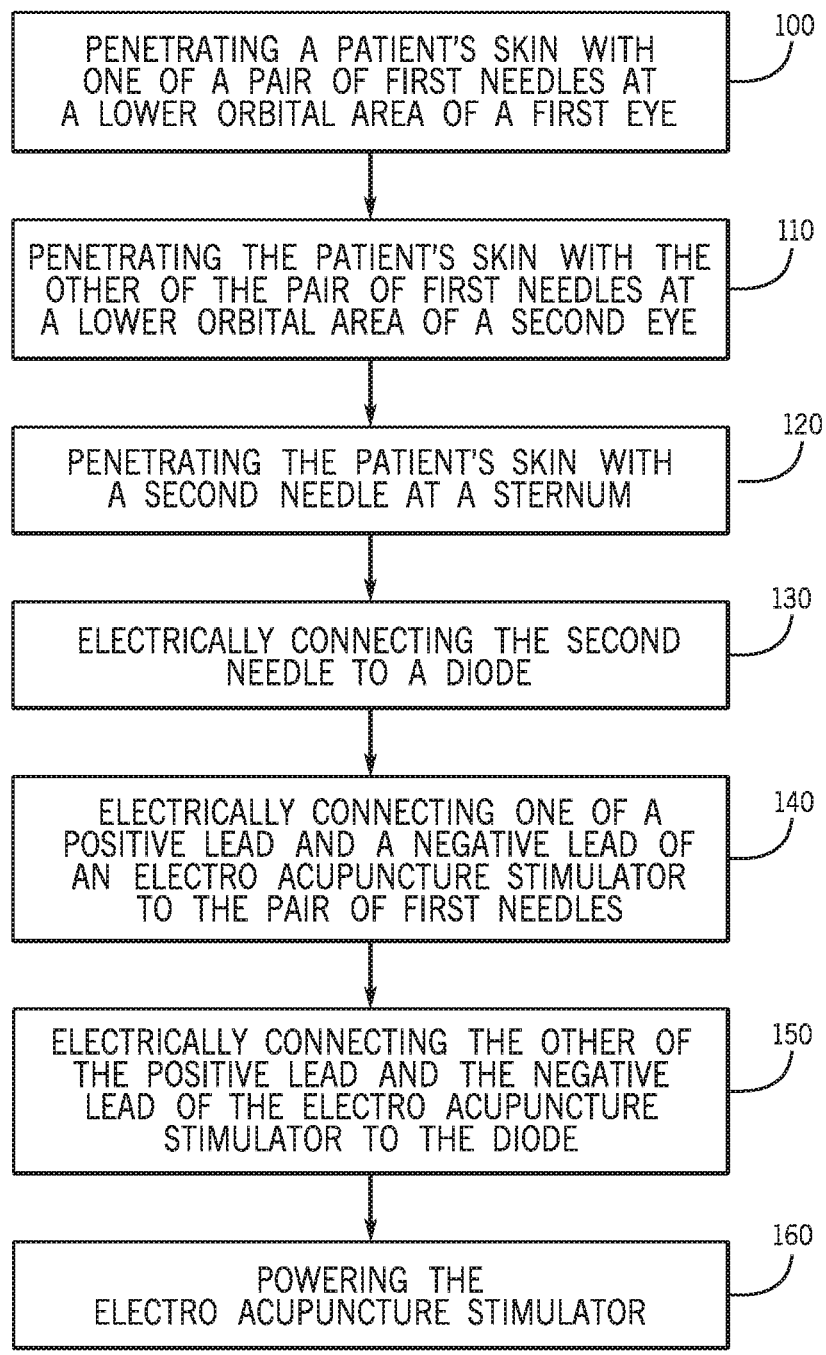
FIG. 3 is a flowchart of an embodiment of a method of the present invention.

Referring to FIG. 1, the present invention includes a system 10 for eye treatment. The system 10 includes an electro acupuncture stimulator 16. The electro acupuncture stimulator 16 includes a positive lead 18 and a negative lead 18. The system 10 further includes a pair of first needles 26a, a second needle 26b and a diode 22. The pair of first needles 26a are electrically connected to one of the positive lead 18 and the negative lead 18. The diode 22 is electrically connected to the other of the positive lead 18 and the negative lead 18. The second needle 26b is electrically connected to the diode 22.

In certain embodiments, the pair of first needles 26a are electrically connected to the positive lead 18 and the diode 22 is electrically connected to the negative lead 18. Alternatively, the pair of first needles 26a are electrically connected to the negative lead 18 and the diode 22 is electrically connected to the positive lead 18.

The electrical connections are made by electrical wiring 20. Electrical wires 20 electrically connect the pair of first needles 26a to the electro acupuncture stimulator 16 by an electrical connector 24, such as a clip, wrapped wires and the like. Electrical wires 20 electrically connect the second needle 26b to the diode 22 by an electrical connector 24. Electrical wires 20 electrically connect the diode 22 to the electro acupuncture stimulator 16.

The pair of first needles 26a may be a pair of needles used to penetrate skin at the lower orbital area 12 of the eye corresponding to BL1 (an acupuncture point). In such embodiments, each of the pair of first needles 26a may include about a 9 mm length and about a 0.12 mm diameter. The second needle 26b may be a needle used to penetrate the skin at the sternum acupuncture point REN 17 14 of a patient. In such embodiments, the second needle 26b may include about a 30 mm length and about a 0.2 mm diameter.

The blocking diode 22 ensures output from electro acupuncture stimulator 16 produces a square wave of positive polarity causing a small oscillation of about 3 hz of the 2 hz stimulation signal base line. The blocking diode 22 converts a full wave to ½ wave while keeping the current in the eye and not the chest.

Referring to FIG. 2, the present invention may further include a method. The method may include the following steps: penetrating a patient's skin with one of a pair of first needles at a lower orbital area of a first eye 100; penetrating the patient's skin with the other of the pair of first needles at a lower orbital area of a second eye 110; penetrating the patient's skin with a second needle at a sternum 120; electrically connecting the second needle to a diode 130; electrically connecting one of a positive lead and a negative lead of an electro acupuncture stimulator to the pair of first needles 140; electrically connecting the other of the positive lead and the negative lead of the electro acupuncture stimulator to the diode 150; and powering the electro acupuncture stimulator 160. The above steps may be performed for about 30 minutes at a time and repeated about every 24 hours.

The pair of first needles may be inserted at a depth to touch an orbital bone of the first eye and the second eye. For example, the depth may be at about 7 mm within the skin. The second needle is at a depth of about 3 mm to about 4 mm within the skin.

The bandwidth of electro acupuncture stimulator is around 400 ms and the amplitude is about 2 milliamps. An electrical supply of the electro acupuncture stimulator is at a frequency of about 2 hz to about 10 hz, about 2 hz to about 5 hz or about 3 hz to about 4 hz.

It should be understood, of course, that the foregoing relates to exemplary embodiments of the invention and that modifications may be made without departing from the spirit and scope of the invention as set forth in the following claims.

What is claimed is:

1. A system for improving low vision caused by retinopathies, comprising:
   a positive lead and a negative lead;
   a first and second needle;
   an electro acupuncture stimulator configured to selectively generate an electrical output having a frequency of about 2 hz to about 10 hz, an amplitude of about 2 milliamps, and a bandwidth of about 400 milliseconds; and
   the electrical output communicated to the positive lead and the negative lead adapted for electrical connection between the first needle positioned at an orbital bone beneath an eye of a patient and the second needle positioned at a sternum bone of the patient.

2. The system of claim 1, further comprising: the first needle electrically connected to one of the positive lead and the negative lead, the first needle dimensioned to penetrate a skin surface of the patient at the lower orbital area of the eye corresponding to a BL1 acupuncture point and contact the orbital bone; and the second needle electrically connected to the other of the positive lead and the negative lead, the second needle dimensioned to penetrate the skin at a REN 17 sternum acupuncture point and contact the sternum.

3. A system of claim 2, further comprising:
   a diode electrically connected between the negative lead and the second needle.

4. A system of claim 2, further comprising:
   a diode electrically connected between the positive lead and the first needle.

5. The system of claim 2, wherein the first needle comprises a length of about a 9 mm and diameter of about 12 mm.

6. The system of claim 2, wherein the second needle comprises a length of about 30 mm and a diameter of about 0.2 mm.

7. The system of claim 1, further comprising electrical wires electrically connecting the pair of first needles and the second needle to the electro acupuncture stimulator.

8. The system of claim 1, wherein the electrical output has a frequency of 2 hz to 5 hz.

9. The system of claim 1, wherein the electrical output has a frequency of 3 hz to 4 hz.

10. A system for improving low vision caused by retinopathies, comprising:
    a positive lead and a negative lead;
    a first and second needle;
    an electro acupuncture stimulator configured to selectively generate an oscillating electrical output having an amplitude of about 2 milliamps, and a bandwidth of about 400 milliseconds; and the electrical output communicated to the positive lead and the negative lead adapted for electrical connection between the first needle positioned at an orbital bone beneath an eye of a patient and the second needle positioned at a sternum bone of the patient.

11. The system of claim 10, further comprising: the first needle electrically connected to one of the positive lead and the negative lead, the first needle dimensioned to penetrate a skin surface of the patient at the lower orbital area of the eye corresponding to a BL1 acupuncture point and contact the orbital bone; and the second needle electrically connected to the other of the positive lead and the negative lead, the second needle dimensioned to penetrate the skin at a REN 17 sternum acupuncture point and contact the sternum.

12. A system of claim 10, further comprising:
    a diode electrically connected between the negative lead and the second needle.

13. A system of claim 10, further comprising:
    a diode electrically connected between the positive lead and the first needle.

14. The system of claim 10, wherein the first needle comprises a length of about a 9 mm and diameter of about 12 mm.

15. The system of claim 10, wherein the second needle comprises a length of about 30 mm and a diameter of about 0.2 mm.

* * * * *